(12) United States Patent
Shioda et al.

(10) Patent No.: US 7,688,079 B2
(45) Date of Patent: Mar. 30, 2010

(54) DETECTING APPARATUS FOR DETECTING MOISTURE CONTENT OF MEDIA STACK

(75) Inventors: Michinori Shioda, Yokohama (JP);
Toshihiko Ouchi, Sagamihara (JP);
Takehiko Kawasaki, Kamakura (JP);
Norio Kaneko, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 425 days.

(21) Appl. No.: 11/671,069

(22) Filed: Feb. 5, 2007

(65) Prior Publication Data
US 2007/0200568 A1 Aug. 30, 2007

(30) Foreign Application Priority Data
Feb. 15, 2006 (JP) .............................. 2006-037766

(51) Int. Cl.
*G01R 27/04* (2006.01)
*G01R 27/32* (2006.01)
*G03G 15/00* (2006.01)

(52) U.S. Cl. .......................... 324/640; 324/643; 399/44

(58) Field of Classification Search ................. 324/640, 324/643; 399/44
See application file for complete search history.

(56) References Cited

U.S. PATENT DOCUMENTS

| | | | |
|---|---|---|---|
| 5,845,529 A * | 12/1998 | Moshe et al. ................... | 73/73 |
| 6,636,704 B2 | 10/2003 | Weaver et al. ................. | 399/23 |
| 7,152,861 B2 | 12/2006 | Kawasaki ..................... | 271/262 |
| 7,239,817 B2 | 7/2007 | Kaneko et al. ................ | 399/45 |
| 2004/0012676 A1 * | 1/2004 | Weiner et al. ............ | 348/207.1 |
| 2004/0086287 A1 * | 5/2004 | Minato ......................... | 399/44 |
| 2005/0271403 A1 * | 12/2005 | Kaneko et al. ................ | 399/44 |
| 2006/0022400 A1 | 2/2006 | Kawasaki et al. ........... | 271/227 |
| 2006/0054842 A1 | 3/2006 | Kawasaki et al. ...... | 250/559.04 |
| 2006/0275045 A1 | 12/2006 | Kawasaki et al. ............. | 399/45 |
| 2007/0023996 A1 | 2/2007 | Kawasaki ..................... | 271/262 |
| 2007/0036567 A1 | 2/2007 | Kawasaki et al. ............. | 399/45 |

FOREIGN PATENT DOCUMENTS

| | | |
|---|---|---|
| JP | 8-137145 | 5/1996 |
| JP | 8-334942 | 12/1996 |

* cited by examiner

*Primary Examiner*—Amy He
(74) *Attorney, Agent, or Firm*—Fitzpatrick, Cella, Harper & Scinto

(57) ABSTRACT

A detecting apparatus for detecting information of at least a portion of a stack of sheet media includes an illuminating unit and a detecting unit. The illuminating unit illuminates a side of the stack of sheet media, or a portion thereof with electromagnetic waves. The detecting unit detects electromagnetic waves transmitted through or reflected by the stack of sheet media, or a portion thereof. The detecting apparatus is adapted to compare information of the electromagnetic waves detected by the detecting unit with information about attenuation of electromagnetic waves due to moisture contained in the sheet medium, and detect information of the moisture content of at least a portion of the stack of sheet media.

12 Claims, 5 Drawing Sheets

DETECTING APPARATUS FOR DETECTING MOISTURE CONTENT OF MEDIA STACK

BACKGROUND OF THE INVENTION

1. Field of the Invention

The present invention relates to a detecting apparatus for detecting moisture content of a stack of sheet media, such as papers, by using electromagnetic waves (hereinafter also referred to as EMW or EM waves), and an image forming apparatus using the detecting apparatus. Particularly, the present invention relates to a detecting apparatus for detecting moisture content of at least a portion of a sheet media stack, by using EM waves at frequency or frequencies including at least a portion of a frequency range from 30 GHz to 30 THz, and an image forming apparatus, such as a printing apparatus, using the detecting apparatus. The EM waves including at least a component in the above frequency range are called terahertz waves in this specification.

2. Description of the Related Background Art

Conventionally, an image forming apparatus, such as a printing apparatus, is likely to be influenced by a change in ambient conditions, such as temperature and humidity. Accordingly, to obtain a stable quality of image under various conditions, a sensor, such as a thermometer or a hygrometer, is disposed around an image forming unit of the apparatus. Information detected by the sensor is fed back to an image forming unit to adjust image forming settings thereof.

In the above method, however, it cannot be said that the sensor detects temperature and moisture with sufficient accuracy. Therefore, it is likely that the image forming unit is inappropriately adjusted.

To cope with the above disadvantage, the following method is proposed (see Japanese Patent Application Laid-Open No. 8(1996)-137145). A method proposed therein uses a detecting apparatus that includes plural light emitting units for emitting light at different frequencies, and a light receiving unit for receiving light emitted from each light emitting unit. The light emitting units are sequentially excited to emit different light, and each light reflected off a measurement object, such as sheet paper, is received by the light receiving unit. Moisture content of the measurement object is estimated based on a comparison result of those received light signals, and image forming settings are adjusted according to the estimated moisture content.

Quite often, however, distribution of moisture content of a paper stack set in a paper holder or tray is not uniform along a paper stacking direction. Moisture contents at upper, central and lower portions of the paper stack may differ from each other. Further, there are also cases where moisture content varies along an in-plane direction of the paper. Hence, moisture content detected by the above method may be that at an upper portion of the paper stack, or that at a portion illuminated with light. Accordingly, especially in a case where printing is performed by a high-speed printer, or other cases where moisture content is required to be detected with greater accuracy, a difference may occur between the measured moisture content of the detected paper and actual moisture content of paper to be printed.

Further, the following methods are also proposed (see Japanese Patent Application Laid-Open No. 8(1996)-334942, and U.S. Patent Application No. 2003/0091351). In those methods, a side of a paper stack is irradiated with light, and paper information is detected. However, the method of the former reference is simply adapted to detect the presence and absence, or quantity of, remaining papers in a paper tray, and the method of the latter reference is only adapted to detect paper thickness. In other words, those methods are not directed to detection of moisture content of paper.

SUMMARY OF THE INVENTION

It is therefore an object of the present invention to provide a detecting apparatus for detecting the moisture content of at least a portion of a sheet media stack, such as a paper stack set in a paper tray, and an image forming apparatus using the detecting apparatus.

According to one aspect of the present invention, there is provided a detecting apparatus for detecting information of at least a portion of a stack of sheet media, which includes an illuminating unit and a detecting unit. The illuminating unit illuminates a side of the stack of sheet media, or a portion thereof, with EM waves. The detecting unit detects EM waves transmitted through or reflected by the stack of sheet media, or a portion thereof. The detecting apparatus is adapted to compare information of the EM waves detected by the detecting unit with information about attenuation of EM waves due to moisture contained in the sheet medium, and determine information of the moisture content of at least a portion of the stack of sheet media.

According to another aspect of the present invention, there is provided an image forming apparatus, which includes the above detecting apparatus, and an image forming unit for forming an image on a record sheet medium. The image forming apparatus is adapted to adjust image forming settings of the image forming unit, based on the moisture content of at least a portion of a stack of record sheet media as detected by the detecting apparatus.

According to the present invention, information of moisture content of a media stack, such as a paper stack, or a portion thereof, can be detected in a flexible manner. More specifically, the information can be accurately detected without contacting the media stack, using EM waves illuminated on a measurement region of the media stack. For example, in the case of a paper stack, it is possible to detect a difference in moisture content at upper, central and lower portions of the media stack. Therefore, in an image forming apparatus, for example, when the information is fed back to image forming settings of an image forming unit, the image forming unit can be adjusted more suitably for the condition of paper.

The features of the present invention will be more readily understood in connection with the following detailed description of the embodiments and examples of the invention in connection with the drawings.

DESCRIPTION OF THE EMBODIMENTS

Embodiments of a detecting apparatus and method for detecting information of at least a portion of a stack of sheet media, such as papers, and an image forming apparatus of the present invention will hereinafter be described with reference to the drawings.

Embodiments of apparatus and method for detecting moisture content of paper by using terahertz waves will be described. Embodiments (especially the embodiment of FIG. 6 described later) can be suitably used in a high-speed printer for rapidly printing a large amount of paper, such as a POD (Print On Demand) machine. Naturally, embodiments can also be used in any other types of printers, and are suitable for detecting moisture content in a desired portion of a paper stack set in a paper tray of a printer, for example.

Figure 1:
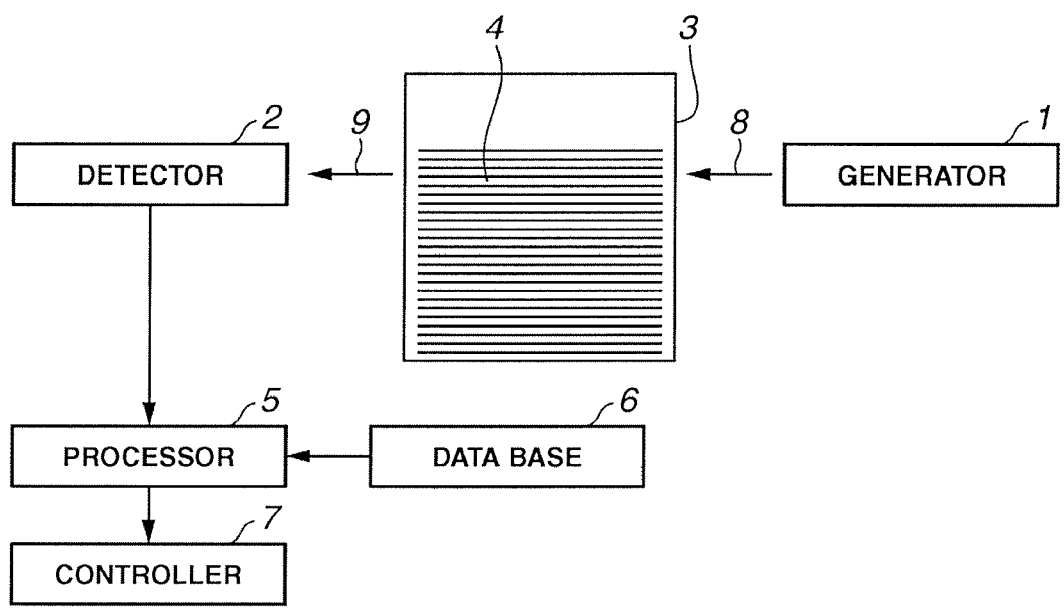
FIG. 1 is a schematic view illustrating a first embodiment of a detecting apparatus according to the present invention, which detects moisture content of at least a portion of a paper stack by using EM waves.
Figure 2:
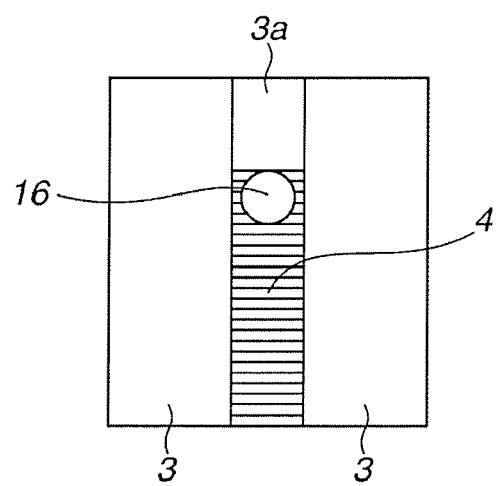
FIG. 2 is a side view, viewed from a side of an EMW generator, illustrating a paper tray for holding a paper stack in FIG. 1.

A first embodiment will be described with reference to FIG. 1. FIG. 1 is a schematic view taken from a side of the apparatus. In the first embodiment, as illustrated in FIG. 1, an EMW generator 1 is arranged near a side of a tray 3 in which a paper stack 4 (a stack of papers 4) is held. A beam of terahertz waves 8 is applied on a portion of a side of the paper stack 4. Terahertz waves 8 can be continuous waves or pulsed waves. Terahertz waves 8 can transmit through the paper 4, and hence, transmission terahertz waves 9 can be detected by an EMW detector 2 disposed near an opposite side of the tray 3. Sides of the tray 3 are provided with openings 3a for permitting illumination terahertz waves 8 and transmission terahertz waves 9 to pass therethrough, respectively (see FIG. 2).

The beam diameter of illumination terahertz waves 8 is adjusted by a lens, a mirror, or the like so that a side of the paper stack 4 or its portion can be illuminated with a beam spot 16 (see FIG. 2) having the same size as a side of a region of the paper stack 4, whose moisture content is required to be detected. Typical beam diameter is about 5 mm. A diameter more than that value is also usable, and the diameter can be about 1 cm, for example.

Figure 3:
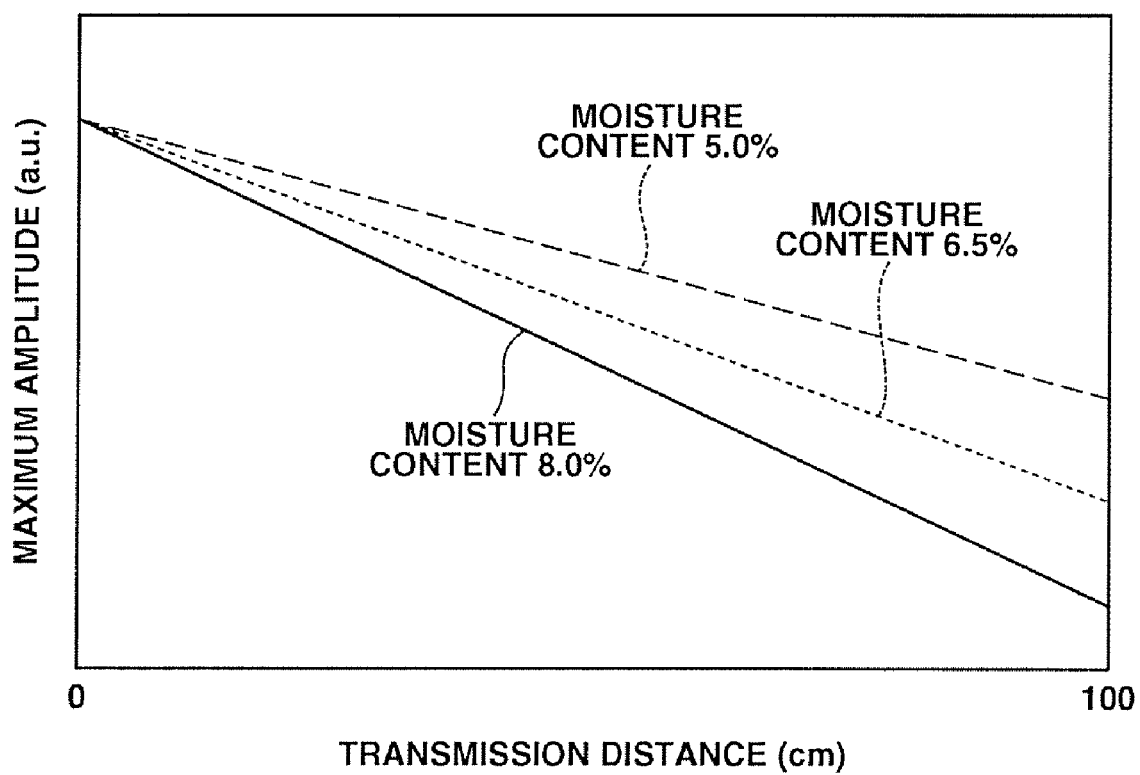
FIG. 3 is a graph showing exemplified calibration curves representing relationships between moisture content of paper, transmission distance of EM waves through paper, and detected maximum amplitude.

In the first embodiment, a calculating processor 5 calculates maximum amplitude from the transmission terahertz waves 9 detected by the EMW detector 2. The maximum amplitude is information of EM waves detected by the EMW detector 2. Such a relationship as illustrated in FIG. 3 exists between the maximum amplitude, the transmission distance of EM waves 8 through the paper 4, and the moisture content of the paper 4. Accordingly, calibration curves representative of the above relationship can be prepared beforehand, and can be used afterward. In other words, when the transmission distance of EM waves 8 through the paper 4 is known, moisture content of the paper 4 (for example, a ratio of the moisture amount relative to the total weight of the paper 4) can be obtained based on a value of the maximum amplitude obtained by the processor 5. In the event that a point concerned does not fall on any calibration curves shown in FIG. 3, the moisture content can be obtained by interpolation, extrapolation, or the like. In FIG. 3, the abscissa represents a linear indication, and the ordinate represents a logarithmic indication. The reason for calculating the maximum amplitude is to increase a signal-to-noise ratio (SN).

Terahertz waves can be easily absorbed by water or moisture, and therefore the relationship as illustrated in FIG. 3 can be obtained. Accordingly, it is desirable that terahertz waves in use include a frequency component that can be readily absorbed by moisture. For example, terahertz waves at frequencies around 1 THz are preferable.

Figure 4:
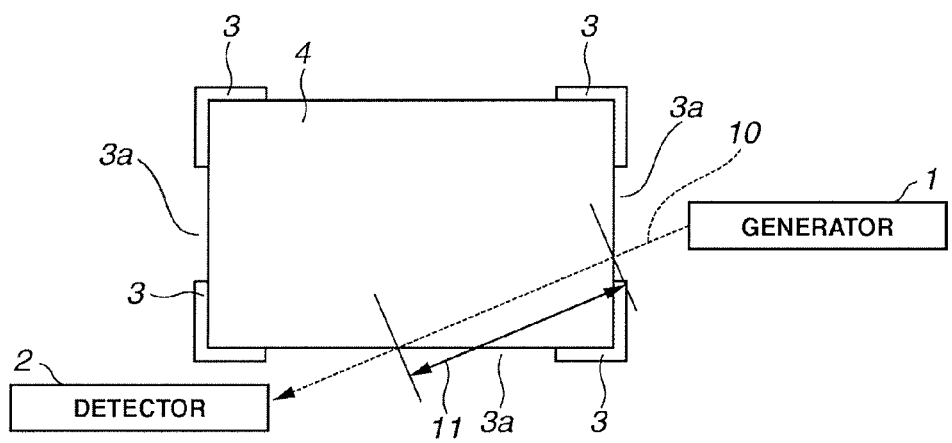
FIG. 4 is a top view illustrating a transmission manner of EM waves through measurement media (papers) in a modification of the first embodiment.

Incident angle of EM waves 8 in a plane of the paper 4 is perpendicular to an edge (a side surface) of the paper stack 4. Alternatively, as illustrated in FIG. 4 viewed from above the paper stack 4, EM waves can be applied obliquely to the side surface of the paper stack 4 as indicated by a path 10 of EM waves. In this case, transmission distance 11 of the EM waves 8 through the paper 4 is shorter than that in a case where EM waves 8 are applied perpendicularly to the side surface of the paper stack 4. Therefore, in the former case, attenuation of EM waves 8 due to the paper 4 can be advantageously reduced. In either case, transmission distance 11 of EM waves 8 through the paper 4 is determined by incident angle and illumination position of the EM waves 8 on the side of the paper stack 4.

Accordingly, the transmission distance 11 can be treated as known parameter. In such an obliquely-illuminating structure, positions of EMW generator 1 and EMW detector 2 can be readily adjusted when a unit structure of EMW generator 1 and EMW detector 2 is provided. Further, when a photoconductive antenna is used as each of EMW generator 1 and EMW detector 2, optical pumping probe system can be reduced in size by forming the photoconductive antennae as a unit. Therefore, the entire size of the structure can be preferably decreased.

Furthermore, it is possible to form such a structure in which a beam of EM waves 8 from EMW generator 1 is caused to be obliquely incident on a side of a media stack, EM waves 8 transmitted through the media stack and reflected by a mirror are again caused to be obliquely incident on another side of the media stack, and EMW detector 2 detects EM waves 8 from the media stack. In this structure, transmission distance through the media stack can be doubled. Therefore, this structure is effective for measuring a stack of small sheet papers, such as post cards. Also in this case, locations of EMW generator 1, EMW detector 2, and mirror can be readily adjusted when a unit structure of EMW generator 1, EMW detector 2, and mirror is provided.

Calibration curves for attenuation data of EM waves 8 due to moisture contained in paper 4 are prepared for respective kinds of papers and stored in data base 6. The operator inputs data on the kind of paper placed in the apparatus at the time of printing. Alternatively, a sensor can be provided to automatically detect the kind of paper. When calibration curve data is stored in data base 6 in the apparatus, the moisture content of paper 4 can be calculated by the calculating processor 5 based on the maximum amplitude of EM waves detected by the EMW detector 2 and data of the calibration curves (see FIG. 1).

The thus-calculated moisture content is the moisture content contained in a portion of the paper stack 4 in the paper tray 3, through which EM waves 8 transmit. As printing proceeds, each top paper 4 of the paper stack 4 in the tray 3 is sequentially supplied to a place, such as a photosensitive drum in an electro-photographic printer. Simultaneously, the paper stack 4 left in the tray 3 is lifted by a lift (not shown) disposed under the tray 3. Therefore, as illustrated in FIG. 1, a portion of the paper stack 4 immediately prior to printing is always illuminated by EM waves 8. Thus, the moisture content of paper 4 immediately prior to printing can be detected.

The detected moisture content of paper 4 immediately prior to printing is fed back to an image forming controller 7 for adjusting image forming settings, such as heating temperature at the time of fixation, and transferring bias voltage of toner at the time of transfer around a photosensitive drum in an image forming apparatus. Thus, adjustment of the image forming unit can be assuredly achieved appropriately to the conditions of paper 4 to be printed.

Figure 5:
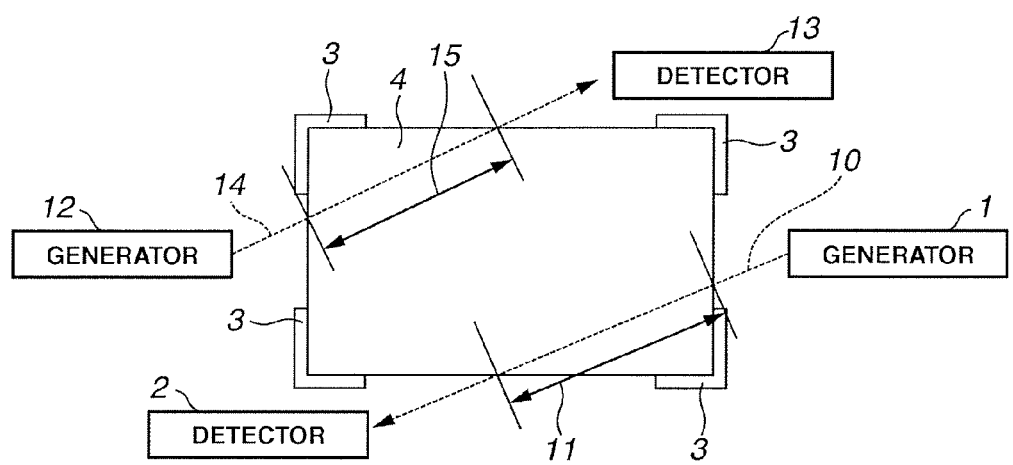
FIG. 5 is a top view illustrating a transmission manner of EM waves through measurement media (papers) in another modification of the first embodiment, using plural beams of EM waves.

In the above-discussed first embodiment, a single set of EMW generator 1 and EMW detector 2 is employed. As illustrated in FIG. 5, however, a plurality of sets (frequencies of all EM waves concerned are the same) of EMW generators 1 and 12, and EMW detectors 2 and 13 can be used. In this modification of the first embodiment, the average of maximum amplitudes detected by respective EMW detectors 2 and 13 can be used to calculate moisture content of paper 4 immediately prior to printing. In another method, maximum amplitude showing the largest moisture content can be used to calculate moisture content of paper 4 immediately prior to printing. According to those structures, moisture content of paper 4 immediately prior to printing can be detected more accurately. In FIG. 5, reference numeral 14 designates a path along which EM waves from the EMW generator 12 propagate, and reference numeral 15 designates transmission distance through paper 4 of EM waves from the EMW generator 12.

In the above description, transmission EM waves are detected. Although attenuation of EM waves due to transmission through paper 4 increases slightly, reflection EM waves reflected by the tray 3 can also be detected to achieve the same purpose. In this structure, the paper tray 3 has no aperture which allows EM waves emitted from EMW generator and transmitted through paper 4 to pass through the tray 3. Thus, EM waves transmitted through paper 4 are reflected by a plate of the paper tray 3 without any aperture, and are again transmitted through paper 4 to be guided to EMW detector. This structure can be applied to the following embodiments, too.

Figure 6:
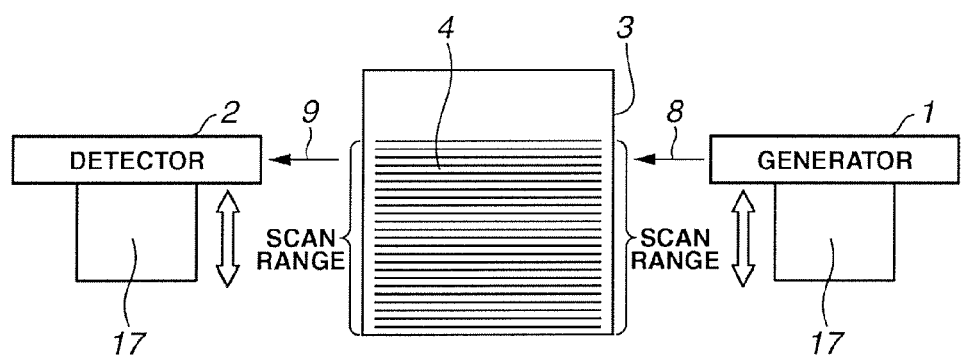
FIG. 6 is a schematic view illustrating a second embodiment of a detecting apparatus according to the present invention, which detects a distribution of moisture content in a stacking direction of a paper stack by using EM waves.

Description will be made for a second embodiment illustrated in FIG. 6. FIG. 6 shows the second embodiment viewed from its side. In the second embodiment, distribution of moisture content of papers 4 in the paper stacking direction is detected by using transmission EM waves 9. In a structure of the second embodiment, in addition to the structure shown in FIG. 1, there are provided stages 17 for synchronously moving EMW generator 1 and EMW detector 2, respectively, in a vertical direction (up and down directions) along a side of paper stack 4. Each stage 17 is disposed at a lower portion of each of EMW generator 1 and EMW detector 2. In another structure, both EMW generator 1 and EMW detector 2 can be disposed on a common stage 17 so that they can be moved in the vertical direction simultaneously.

In the second embodiment, prior to printing, EMW generator 1 and EMW detector 2 are moved vertically over a given scan range of paper stack 4 held in the tray 3. Maximum amplitude obtained from transmission EM waves 9 detected by EMW detector 2 at each scan position, and the scan positions are stored in a memory. Transmission distance of EM waves 8 through paper 4 is known. Therefore, moisture content of paper 4 at each scan position can be obtained from the above maximum amplitude, using calibration curves as illustrated in FIG. 3, in the same manner as the first embodiment. Thus, moisture content of paper 4 at each scan position in the stacking direction of paper stack 4 can be acquired. Consequently, distribution of moisture content in the stacking direction of paper stack 4 can be detected.

The number of papers 4 set in the tray 3 is input into the apparatus by an operator. Alternatively, a sensor can be provided to detect the number of papers 4. When printing is started in this state, the number of printed papers can be known from an indication of a counter provided in the printer. Accordingly, the number of papers 4 remaining in the tray 3 after printing can be counted. From the number of papers 4 left in the tray 3, the position of paper 4 immediately prior to the next printing in the stacking direction can be calculated. Hence, moisture content of paper 4 immediately prior to printing can be known from the relationship between the position of paper 4 in the stacking direction and moisture content of paper 4 thereat.

Also in the second embodiment, the detected moisture content of paper 4 immediately prior to printing is fed back to the image forming controller 7 for adjusting image forming settings, such as heating temperature at the time of fixation, and transferring bias voltage of toner at the time of transfer. It is thus possible to adjust the image forming settings more appropriately to the condition of paper 4 immediately prior to printing.

In the second embodiment, when distribution of moisture content of papers 4 in the stacking direction is detected, EMW generator 1 and EMW detector 2 are moved by the stage 17. During the detecting operation, moisture content of paper 4 can be periodically calculated by using calibration curves as illustrated in FIG. 3. By comparing the calculated moisture content with humidity detected by a hygrometer disposed near the apparatus, the length of time that has elapsed after papers 4 are set in the tray 3 can be estimated. In the event that a short period of time has elapsed after papers 4 are set in the tray 3, scanning by the stage 17 continues to obtain the distribution of moisture content of papers 4 in the stacking direction. When a sufficiently long period of time has passed after papers 4 have been set in the tray 3, conditions of papers 4 can be considered to be sufficiently in accord with the atmosphere. Accordingly, moisture content of papers 4 can be considered substantially the same throughout the stacking direction of the paper stack 4. In other words, the distribution of moisture content of papers 4 in the stacking direction can be considered to be uniform and equal to the above calculated one. Hence, the scan by the stage 17 can be stopped.

Figure 7:
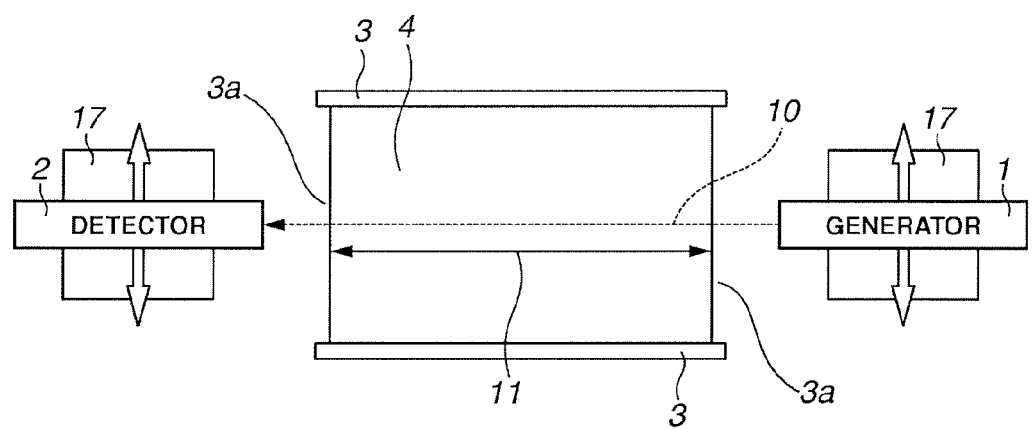
FIG. 7 is a schematic top view illustrating a third embodiment of a detecting apparatus according to the present invention, which detects a distribution of moisture content in an in-plane direction of a paper stack by using EM waves.

Description will be made for a third embodiment shown in FIG. 7. FIG. 7 shows the third embodiment viewed from above of a portion of the printer. Construction of the third embodiment is basically the same as that of the second embodiment. The third embodiment differs from the second embodiment in that EMW generator 1 and EMW detector 2 are synchronously moved by stages 17 in a horizontal direction relative to papers 4 (up and down directions in FIG. 7) along a side of the paper stack 4. Each stage 17 is disposed below each of EMW generator 1 and EMW detector 2. Path of EM waves from the EMW generator 1 through the paper stack 4 is perpendicular to a side of the paper stack 4. Also in this structure, EMW generator 1 and EMW detector 2 can be disposed on a common stage 17 so that they can be moved in the horizontal direction simultaneously.

Figure 8:
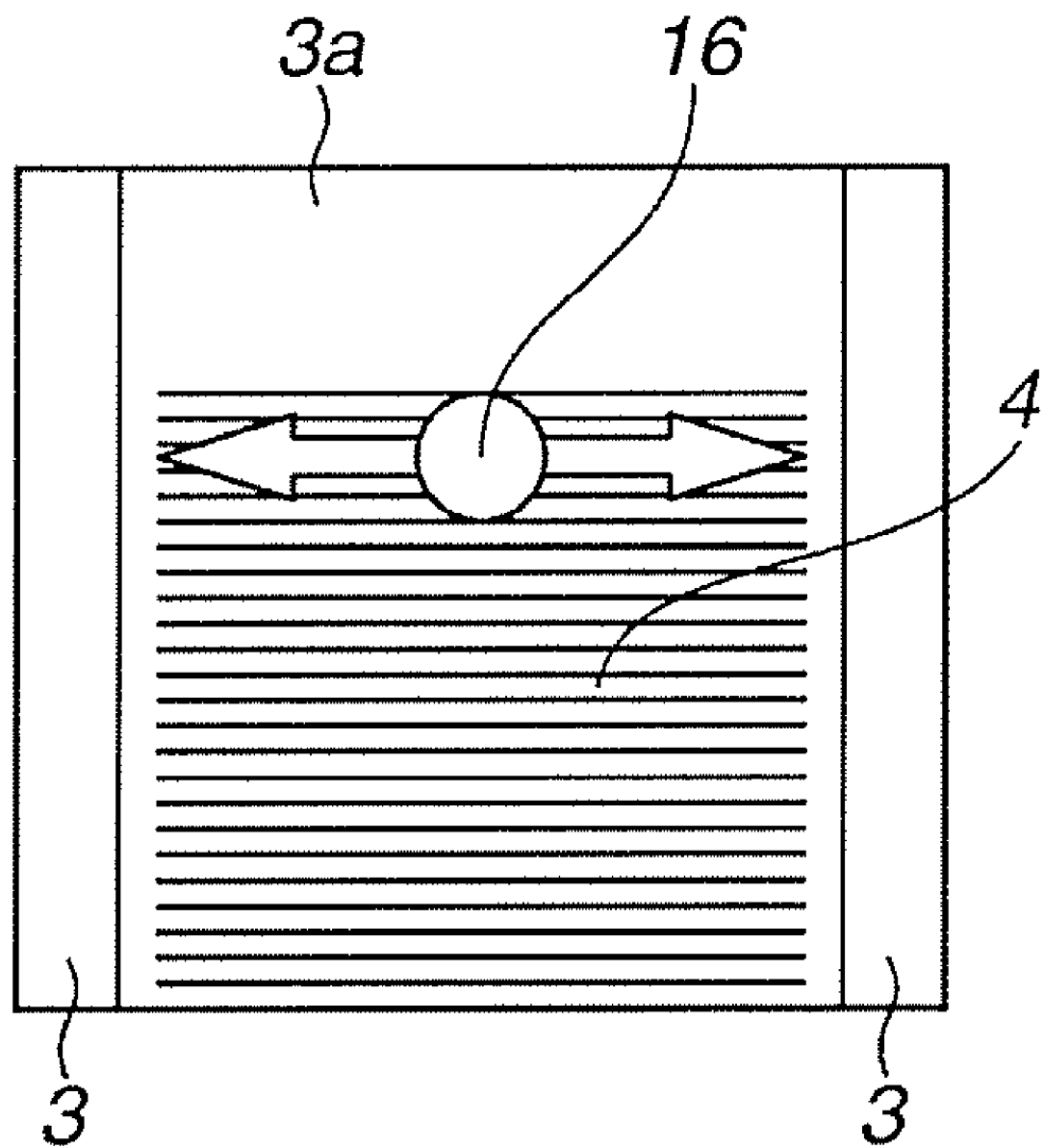
FIG. 8 is a side view, viewed from a side of an EMW generator, illustrating a paper tray for holding a paper stack in FIG. 7.

FIG. 8 viewed from a side of the EMW generator 1 illustrates the paper stack 4 held in the paper tray 3. When the stage 17 is moved in the horizontal direction, an illumination spot 16 on the paper stack 4 is scanned in rightward and leftward directions as viewed in FIG. 8. Tray 3 is configured so that the illumination spot 16 of EM waves 8 from the EMW generator 1 cannot be blocked by the paper tray 3. Specifically, a wide opening 3a is formed in each side plate of the tray 3, as illustrated in FIGS. 7 and 8.

In a state wherein the paper stack 4 is set in the tray 3, EMW generator 1 and EMW detector 2 are moved over a given scan range in the horizontal direction prior to printing. Maximum amplitude of transmission EM waves 9 detected by the EMW detector 2 at each scan position, and the scan positions are stored in a memory. Transmission distance 11 of EM waves 8 through the paper stack 4 is known. Therefore, moisture content of paper 4 can be obtained from the maximum amplitude, using calibration curves of FIG. 3, in the same manner as the first embodiment. Thus, moisture content of paper 4 at each horizontal scan position can be obtained. Consequently, an in-plane distribution of moisture content of sheet paper 4 can be detected. Average moisture content can be acquired from the thus-obtained in-plane distribution of moisture content. This average moisture content can be used as the moisture content of the paper 4 concerned.

Also in the third embodiment, the detected moisture content of paper 4 immediately prior to printing is fed back to the image forming controller 7. It is thus possible to adjust the image forming settings more appropriately to the condition of paper 4 immediately prior to printing.

Except as otherwise disclosed herein, the various components shown in outline or in block form in the figures are individually well-known and their internal construction and operation are not critical either to the making or using of the present invention or to a description of the best mode of the invention.

While the present invention has been described with respect to what is presently considered to be the embodiments and examples, it is to be understood that the invention is not limited to the disclosed embodiments and examples. The present invention is intended to cover various modifications and equivalent arrangements included within the spirit and the scope of the appended claims.

This application claims priority from Japanese Patent Application No. 2006-037766, filed Feb. 15, 2006, the contents of which are hereby incorporated by reference.

What is claimed is:

1. An image forming apparatus which comprises an image forming unit for forming an image on a record sheet medium and a detecting apparatus for detecting moisture content of at least a portion of a stack of sheet media, the detecting apparatus comprising:
   an illuminating unit for illuminating a side of at least a portion of the stack of sheet media with electromagnetic waves;
   a detecting unit for detecting electromagnetic waves transmitted through or reflected by at least a portion of the stack of sheet media;
   a memory for storing information about attenuation of electromagnetic waves due to moisture contained in a sheet material; and
   a comparator for comparing information of the electromagnetic waves detected by the detecting unit with the information in the memory about attenuation of electromagnetic waves due to moisture contained in the sheet medium, and determining moisture content of at least a portion of the stack of sheet media,
   wherein the information stored in the memory is stored calibration curves, and a maximum amplitude of the transmitted or reflected electromagnetic waves detected by the detecting unit is compared with the stored calibration curves, and
   wherein the calibration curves are composed of three parameters; transmission distance of the electromagnetic waves through at least a portion of the stack of sheet media, maximum amplitude of the transmitted or reflected electromagnetic waves detected by the detecting unit, and moisture content of the sheet medium.

2. The image forming apparatus according to claim 1, wherein a plurality of sets of illuminating units and detecting units are provided to detect electromagnetic waves transmitted through or reflected by at least a portion of the stack of sheet media, respectively, the plurality of sets of illuminating units and detecting units being arranged such that the transmission distances in these sets are different from each other.

3. The image forming apparatus according to claim 1, wherein the illuminating unit and detecting unit are each movable in a vertical direction along a side of the stack of sheet media to detect information of a distribution of moisture content of at least a portion of the stack of sheet media along the vertical direction.

4. The image forming apparatus according to claim 1, wherein the illuminating unit and detecting unit are movable in a horizontal direction along a side of the stack of sheet media to detect information of a distribution of moisture content of at least a portion of the stack of sheet media along a direction perpendicular to a stacking direction.

5. The image forming apparatus according to claim 1, wherein the electromagnetic waves contain at least a component at frequency or frequencies in a frequency range between 30 GHz and 30 THz, which can be absorbed by moisture.

6. The image forming apparatus according to claim 1, wherein a spot of the electromagnetic waves is adjusted to have the same size as a side or a region of the stack of sheet media.

7. The image forming apparatus according to claim 1, further comprising a tray for storing a stack of sheet media;
   wherein the illuminating unit generates electromagnetic waves containing at least a component at frequency or frequencies in a frequency range between 30 GHz and 30 THz in an in-plane direction of the sheet media and illuminates a predetermined position of a side of the stack of sheet media with the generated electromagnetic waves at a predetermined angle within a plane of the sheet media with respect to the in-plane direction of the sheet media stored in the tray.

8. An image forming apparatus according to claim 1, wherein the transmission distance is determined by incident angle and illumination position of the electromagnetic waves on the side of the stack of sheet media.

9. An image forming apparatus comprising:
   a storing unit for storing a stack of sheet media;
   a position determining unit for determining a position in a side of the stack of sheet media stored in the storing unit;
   an angle determining unit for determining an angle within a plane of the sheet media with respect to an in-plane direction of the sheet media stored in the storing unit;
   an illuminating unit including a generation unit for generating electromagnetic waves containing at least a component at frequency or frequencies in a frequency range between 30 GHz and 30 THz in an in-plane direction of the sheet media, the illuminating unit illuminating the position determined by the position determining unit with the electromagnetic waves generated by the generating unit at the angle determined by the angle determining unit;
   a detecting unit for detecting an intensity of the electromagnetic waves transmitted through the stack of sheet media or an intensity of the electromagnetic waves transmitted through the stack of sheet media and reflected by a side surface of the storing unit among the electromagnetic waves generated from the illuminating unit;

a transmission distance obtaining unit for obtaining a transmission distance of the electromagnetic waves through the stack of sheet media by using the determined position and angle;

a memory for storing information about attenuation of electromagnetic waves due to moisture contained in sheet media;

a moisture content obtaining unit for obtaining moisture content contained in the stack of sheet media stored in the storing unit by using the transmission distance obtained by the transmission distance obtaining unit and the information about attenuation; and an image forming unit for forming an image on the sheet media.

10. An image forming apparatus according to claim 9, wherein the storing unit is a tray.

11. An image forming apparatus according to claim 9, further comprising:

a unit for changing a relative position between the illuminating unit and the detecting unit, and the storing unit in a vertical direction along the side of the stack of sheet media; and a counting unit for counting a number of the sheet media in the stack stored in the storing unit, wherein a predetermined position of the sheet media in a stacking direction is obtained by using the counted number of the stacked sheet media.

12. An image forming apparatus according to claim 11, wherein the counting unit includes a counter for counting a number of used sheet media and subtracts the number of used sheet media counted by the counter from a number of the stacked sheet media which was input when the stack of sheet media was stored in the storing unit.

* * * * *